March 14, 1939. J. J. GRULLEMANS Plant Pat. 318
KNIPHOFIA OR TRITOMA
Filed Aug. 12, 1938
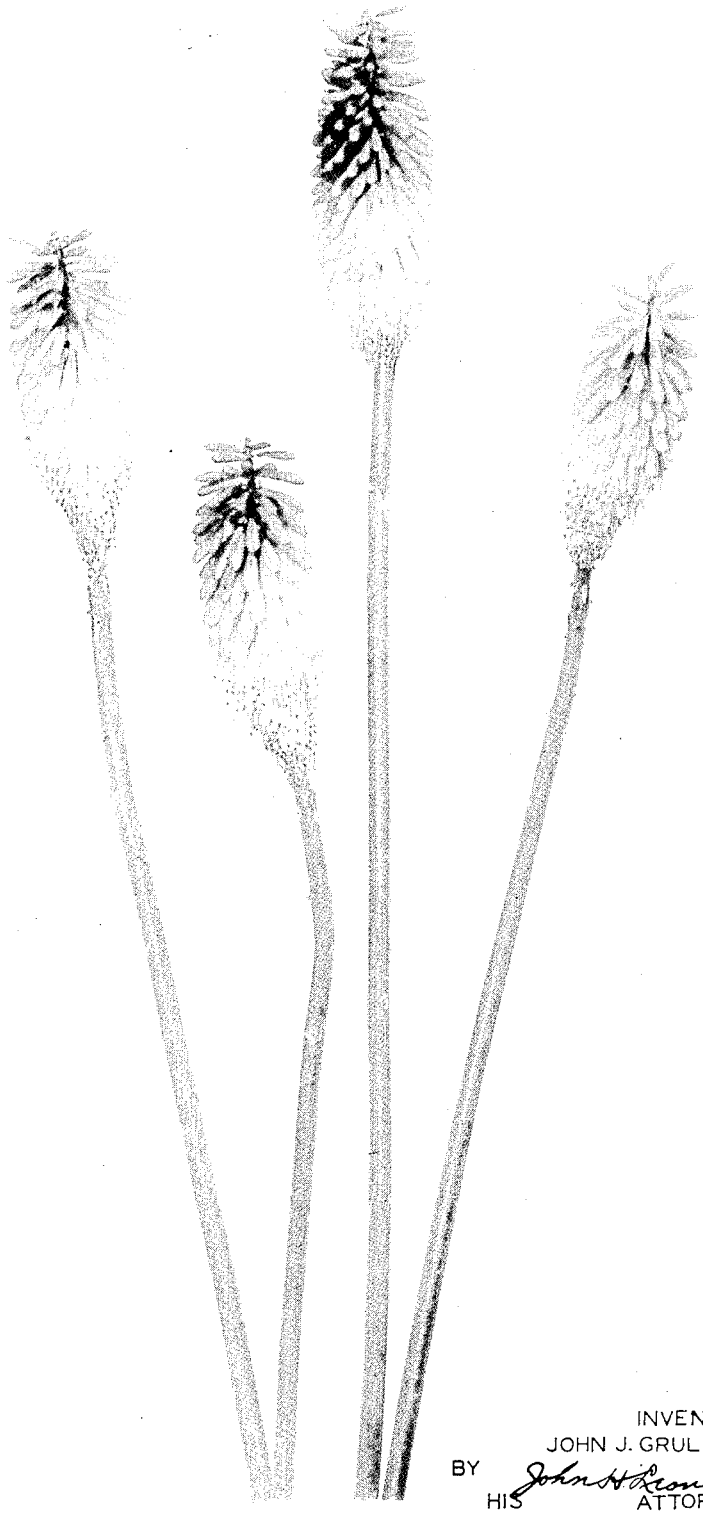
INVENTOR
JOHN J. GRULLEMANS
BY John H. Leonard,
HIS ATTORNEY Patented Mar. 14, 1939

Plant Pat. 318

UNITED STATES PATENT OFFICE

318

KNIPHOFIA OR TRITOMA

John James Grullemans, Mentor, Ohio, assignor to Wayside Gardens Company, Mentor, Ohio, a corporation of Ohio Application August 12, 1938, Serial No. 224,528

1 Claim. (Cl. 47—60)

This invention relates to a new and distinct variety of kniphofia plant, commonly termed "tritoma", and having as a primary object the origination of a hardy variety of kniphofia plant which begins to bloom comparatively early in the growing season, that is, during the month of June, and in a very profuse manner, bearing spikes or racemes of a distinctive coloring.

In producing this new variety, I crossed as the seed bearer or the male parent, "*Kniphofia quartiniana*", characterized for its hardiness and early blooming of complete yellow flowers on a very stout peduncle, with "*Kniphofia uvaria grandiflora*" as the female parent, which is distinctive for its hardiness and its flowers, with an upper portion of red and a lower portion of yellow, produced during the late summer or early fall. A plant of this crossing was then recrossed, as the female parent, with a hybrid variety "*Kniphofia rufa*" as the male parent. Since the original production of the new variety, many plants have been asexually reproduced, and each of them has borne flowers true to the description herein made.

This new variety of kniphofia plant produces flowers in a very profuse manner, that is, some fifteen to twenty flower spikes are borne on a plant of two years' growth. These spikes or racemes are densely headed with individual drooping tubular flowers. The upper portion of these flower spikes, substantially the upper one-half of the spike, is of a coral red color, approaching Maerz & Paul Plate No. 3–L–10, and the lower portion or remainder of the spike is of a white color, between a creamy and an ivory white and approaching Maerz & Paul "Polar Bear", Plate No. 9–B–2. As these spikes or racemes grow older or develop, the coral red portion changes to a white color substantially like the white petals of the lower portion. These blooms illustrated in the drawing show a varied extent of red colored portion as compared with the white portion since some of the blooms are more developed as compared with the others. This change of color of the individual flowers continues until just a trace of the coral red is present at the very tip of the flower spike. An advantage in the new variety is the usefulness of the flowers for decorative purposes, both while growing and when used as a cut flower.

Each of the flower spikes is supported by a stout peduncle having a green color like that of the foliage, approaching Maerz & Paul Plate No. 23–L–7. The foliage consists of leaves having ensiform-acuminate shape, each being about two to three feet long and about one inch or less in breadth, with the ends tapering into a long point. The foliage borne by the plant is much like that of the "Quartiniana" variety, both as to its color and to the dense basal rosette formation, and accordingly the drawing does not illustrate the foliage of this new variety.

The flower spike and peduncle grow to a height of about 36 inches or more, and due to the strength of the peduncle, the flowers are maintained throughout the flowering season in a substantially erect position. The dark colored stamens, approaching the coral red color of the flowers, form first near the base of the flower spike and progress upwardly as the bloom ages, this stamen coloring blending very well with the coral red of the upper portion, and the lengths of the flower spikes compare favorably with and no doubt are influenced by the "Uvaria" genus in that they vary from four to eight inches in length and each of the spikes contains perhaps 100 of the individual tubular drooping flowers.

The following is a somewhat more detailed description of the new variety and particularly the flower growth and character.

Parentage (seedling):
- *Seed parent.*—*Kniphofia quartiniana.*
- *Pollen parent.*—*Kniphofia uvaria grandiflora.*
- *Recrossed with.*—*Kniphofia rufa*—hybrid pollen parent.

Classification:
- *Botanic and commercial.*—Kniphofia—tritoma.

*Flower*

Blooming habit:
- Location where observations were made: The Wayside Gardens Co., Mentor, Ohio. June-July flowering. Scattered blooms as early as late May.

Bloom:
- *Size.*—4 inches to 4½ inches long.
- *Borne.*—Upright.
- *Stems.*—Straight, 3 to 4 feet long.
- *Permanence.*—Lasting 10 to 14 days.

Color:
- *Upper flower.*—Brilliant coral red.
- *Lower half of flower.*—Cream to ivory white.
- *General tonality from a distance.*—Red and white. Upper half of flower changes color to lower half as flower ages, with the result that flowers are practically all white at the end of their blooming period, except for the very tip of the flower, which remains a coral red.

Variations:
- None.

Discoloration, general tonality:
- None, except for the heretofore described color change.

Fragrance:
- None.

Lasting quality:
- On the plant—10 to 14 days.
- As cut flower—7 to 8 days.

Having now fully shown and described my new kniphofia, and the mode of its production, what I claim and desire to secure by Letters Patent of the United States is:

A new and distinct variety of kniphofia plant as described and characterized by its hardiness and its relatively early and profuse flowering habit of bearing spikes having a substantial upper portion of coral red flowers and the remaining portion of white flowers, which coral red portion of the spike changes in part to white during the development of the spike until a trace of coral red color remains at its tip.

JOHN JAMES GRULLEMANS.